(12) United States Patent
Forouhi et al.

(10) Patent No.: US 6,594,025 B2
(45) Date of Patent: Jul. 15, 2003

(54) METHOD OF MONITORING THIN-FILM PROCESSES AND METROLOGY TOOL THEREOF

(75) Inventors: Abdul Rahim Forouhi, Cupertino, CA (US); Dale A. Harrison, Tracy, CA (US); Eric Maiken, Santa Clara, CA (US); John C. Lam, San Jose, CA (US)

(73) Assignee: N&K Technology. Inc., Santa Clara, CA (US)

( * ) Notice: Subject to any disclaimer, the term of this patent is extended or adjusted under 35 U.S.C. 154(b) by 18 days.

(21) Appl. No.: 09/905,749

(22) Filed: Jul. 12, 2001

(65) Prior Publication Data

US 2003/0053081 A1 Mar. 20, 2003

(Under 37 CFR 1.47)

(51) Int. Cl.$^7$ .......................... G01B 11/28; G01B 11/06
(52) U.S. Cl. ....................... 356/630; 356/382; 356/503; 356/504
(58) Field of Search ................................ 356/382, 503, 356/504, 630

(56) References Cited

U.S. PATENT DOCUMENTS

| | | | |
|---|---|---|---|
| 4,905,170 A | 2/1990 | Forouhi et al. | 364/556 |
| 5,835,226 A | * 11/1998 | Berman et al. | 356/382 |

OTHER PUBLICATIONS

F. Yang,, W. A. McGahan, C. E. Mohler, L. M. Booms; "Optical metrology for monitoring the cure of silk low–k dielectric thin film;" Advanced Metallization Conference (AMC) 1999, Orlando, Florida.

D. A. Harrison, J. C. Lam, G. G. Li, A. R. Forouhi, and G. Dao; "Modeling of optical constants of materials comprising photolithographic masks in the VUV;" Proceeding of the SPIE– 19th Annual BACUS Symposium on Photomask Technology and Management, Sep. 15–17, 1999, Monterey, California USA.

"Etch and integration issues related to low–k materials;" semiconbay.com, Expert viewpoint, May 10, 2000, 11:00 am PST.

Dr. Jerzy Ruzyllo "Search for high–k dielectrics for next generation MOS gates;" semiconbay.com, Editorial.

* cited by examiner

Primary Examiner—Scott J. Sugarman
(74) Attorney, Agent, or Firm—Lumen Intellectual Property Services, Inc.

(57) ABSTRACT

The present invention provides a method for monitoring a modifying-process taking place in a thin-film sample and thereby characterizing the sample thus modified, wherein the modifying-process is performed for purpose of improving physical properties of the sample. The present invention further provides a monitoring tool for characterizing various thin-film processes. Advantages of the method of the present invention are manifest in its non-intrusive nature, fast (or real-time) response, robust sensitivity, and versatility in a variety of thin-film processes. Another inherent advantage of the present invention is that an assortment of the "n&k" parameters can be obtained by using only measurement tool, in contrast to two (or more) simultaneous measurement tools used in the prior art.

22 Claims, 2 Drawing Sheets

METHOD OF MONITORING THIN-FILM PROCESSES AND METROLOGY TOOL THEREOF

FIELD OF THE INVENTION

This invention relates to optical metrology of materials. More specifically, it provides a novel method and metrology tool for monitoring and characterizing thin films, such as low-k dielectric films.

BACKGROUND

As ultra-large-scale-integrated (ULSI) circuits continue shrinking in size to meet ever growing demand for higher performance, the industry is moving toward interconnect technology based on using Cu for metallization and low-κ materials for inter-layer dielectrics. The need for the latter stems from the fact that the capacitance of the interlayer dielectric has become an increasingly limiting factor on the overall performance of ULSI chips. Successful adoption of these newer materials and process technologies requires effective monitoring methods for various film structures and processes. The introduction of new interconnect technology also imposes new challenges and unique requirements. Accordingly, effects have been undertaken in the industry to develop metrology tools for these applications.

Take SiLK dielectric for example. This is a dielectric material under the trade-name by Dow Chemicals. Amongst various candidate materials for low-κ inter-layer dielectric (ILD) applications, SiLK appears to be one of the most promising. SiLK dielectric thin films can be readily produced by way of deposition using conventional spin-coaters. Like other spin-on candidate materials, mechanical, thermal, and electrical properties of SiLK thin films depend upon the degree of cure, during which a polymerization process is thermally activated. Hence, a precise control of the curing temperature and the curing time in real time is critical to the quality of the SiLK dielectric films thus produced.

Yang et al. in "Optical Metrology for Monitoring the cure of SiLK Low-κ Dielectric Thin Films", Advanced Metalization Conference (AMC), Orlando, Fla. 1999, described a method for characterizing SiLK thin films by a combination of spectroscopic reflectometry and ellipsometry techniques. The authors found that at the wavelength of 314 nm, indices of refraction, $n(\lambda)$, of the SiLK thin films change systematically with the curing parameters such as the curing time and curing temperature.

A method that has proved to be particularly effective in characterizing the optical properties of thin films is the so-called "n&k" method. This is a measurement technique that simultaneously determines the thickness d, spectra of physical constants—namely, index of refraction n and extinction coefficient k, energy band-gap $E_g$, and interface roughness σ of thin films deposited on opague or transparent substrates. At the core of the "n&k" method are the original Forouhi-Bloomer dispersion equations for n and k, as described in U.S. Pat. 4,905,170. It is valid from the vacuum-ultra-violet (VUV) to the near-infra-red (NIR) range in spectrum. The high versatility and non-intrusive nature of the "n&k" method makes it applicable to a broad range of semiconductor, dielectric and thin metal films. An important advantage of the "n&k" method from a practical standpoint is that it can provide a variety of physical constants of a thin film by requiring only one measurement technique, such as reflectometry or transmittance, as opposed to two simultaneous techniques in the case of Yang et al. described above.

In the interconnect technology applications involving the use of Cu, the presence of copper oxides can degrade adhesion between copper and silicon nitride. Thus, the oxidation state of copper needs to be monitored. Given that there is a substantial difference between the optical properties of copper, cuprous oxide, and cupric oxide, the "n&k" method can be used to monitor the presence of either a single phase or mixture phases in copper.

As thin-film fabrication and characterization become an increasingly indispensable part of modern technology, there is a need in the art for a non-intrusive, sensitive and robust monitoring tool that can characterize a variety of thin-film processes in an accurate and real-time fashion.

SUMMARY OF THE INVENTION

The present invention provides a method for monitoring a modifying-process taking place in a thin-film sample and thereby characterizing the sample thus modified, wherein the modifying-process is introduced for purpose of improving physical properties of the sample. The present invention further provides a monitoring tool for characterizing various thin-film processes.

In the method of the present invention, a modifying-process is introduced to a thin-film sample; an observing spectral range is identified, in which one or more sensitive "n&k" parameters display pronounced changes in response to the modifying-process; and these sensitive "n&k" parameters are then used to monitor the modifying-process and thereby characterize the effects of the modifying-process on the physical properties of the sample.

In this specification and appending claims, a modifying-process should be construed as a process carried out in a thin-film sample for purpose of modifying and improving one or more physical properties of the sample. The "n&k" parameters include index of refraction n, extinction coefficient k, thickness d, energy band-gap $E_g$, and interface roughness σ of a thin-film sample, as determined by the "n&k" method.

As a way of example, the modifying-process can be a curing process in a thermal-activated polymer film such as a SiLK dielectric film, controlled by the curing temperature and the curing time. The energy band-gap $E_g$ and the spectra of extinction coefficient $k=k(\lambda)$ of a SiLK dielectric film exhibit pronounced changes with the curing temperature and curing time. The spectra of extinction coefficient K appears to be particularly sensitive to the curing temperature and curing time in the wavelength range of 320–370 nm. As such, the energy band-gap $E_g$ and extinction coefficient K provide sensitive "indicators" of the underlying curing process taking place in a SiLK dielectric film.

The method of the present invention has advantages of being non-intrusive, real-time, sensitive, and versatile. Another inherent advantage of the present invention is that an assortment of the "n&k" parameters can be obtained by using only a single measurement tool, in contrast to two (or more) simultaneous measurement tools used in the prior art.

The novel features of this invention, its objects and advantages will become apparent from the following description and accompanying drawings.

DETAILED DESCRIPTION

Figure 1:
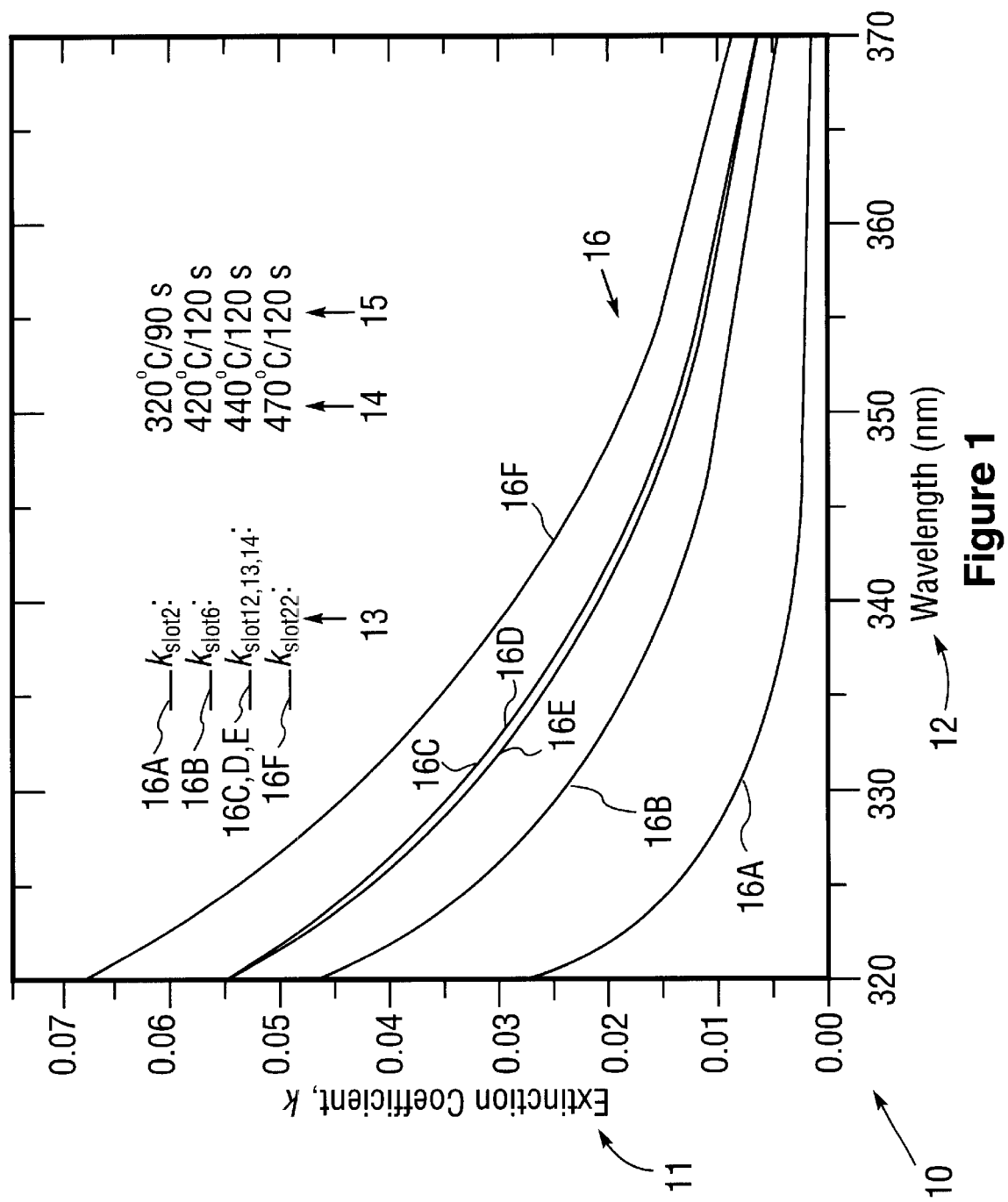
FIG. 1 shows a plot of extinction coefficient k as a function of wavelength λ in the ultra-violet (UV) spectral range for six SiLK dielectric films processed by varying curing temperatures and curing times.

Although the following detailed description contains many specific details for the purposes of illustration, anyone of ordinary skill in the art will appreciate that many variations and alterations to the following details are within the scope of the present invention. Accordingly, the exemplary embodiment of the present invention described below is set forth without any loss of generality to, and without imposing limitations upon, the claimed invention.

For the purpose of elucidating the principle of the present invention, the underlying principle of the "n&k" method is briefly described below. A more detailed description is provided in U.S. Pat. No. 4,905,107, which is incorporated herein by reference for all purposes.

Both n and k are generally functions of wavelength $\lambda$, i.e., $n=n(\lambda)$ and $k=k(\lambda)$. Since $\lambda$ is related to photon energy E, according to $E=hc/\lambda$ (where h is Planck's constant and c is the speed of light in vacuum), n and k can also be described as functions of photon energy E, i.e., $n=n(E)$ and $k=k(E)$. The underpinning factor that relates $n=n(E)$ to $k=k(E)$ is the Kramers-Kronig dispersion relation, which dictates that $n=n(E)$ be determined as the Hilbert transformation of $k=k(E)$. Hence, a viable description of $n=n(E)$ and $k=k(E)$ should be consistent with the Kramers-Kronig dispersion relation.

In practice, $n=n(\lambda)$ and $k=k(\lambda)$ spectra are discursively determined from measurements of optical quantities, such as reflectance R and transmittance T. U.S. Pat. No. 4,905,170 by Forouhi and Bloomer discloses a method for determining these spectra from the reflectance spectrum of a thin film. Their method centers on a formulation for the optical constants $n=n(E)$ and $k=k(E)$, which has been termed as the Forouhi-Bloomer dispersion equations in the art, shown as:

$$k(E) = \sum_{i=1}^{q} \frac{A_i(E-E_g)^2}{E^2 - B_i E + C_i} \quad (1)$$

$$n(E) = n(\infty) + \sum_{i=1}^{q} \frac{B_{oi}E + C_{oi}}{E^2 - B_i E + C_i} \quad (2)$$

In the above equations, the integer q specifies the number of terms involved in the respective sums. Each term in the sum for $n=n(E)$ and for $k=k(E)$ contributes either a peak or a shoulder in their respective spectra. The first term (q=1) describes the spectra of an amorphous material. Polycrystalline or crystalline materials are represented by higher order terms. $E_g$ represents the optical energy band-gap. The parameters $A_i$, $B_i$ and $C_i$ are directly related to the electronic configuration of the material. The parameter $n(\infty)$ represents the lim of $n=n(E)$ as $E \to \infty$ (or $\lambda \to 0$). The parameters $B_{oi}$ and $C_{oi}$ are functions of $A_i$, $B_i$, $C_i$, and $E_g$. Note that Eq. (2) for $n=n(E)$ is derived from Eq. (1) for $k=k(E)$ by way of the Kramers-Kronig dispersion relation.

The Forouhi-Bloom model incorporates the above equations into the Fresnel coefficients, along with a factor dependent on interface roughness, to generate algorithms that describe the calculated (or theoretical) reflectance R or transmittance T of single or multi-layer films. By comparing measurements of R or T with the theoretical predictions and use of a least squares fitting routine, $n=n(\lambda)$ and $k=k(\lambda)$ spectra, film thickness d, energy band-gap $E_g$, and interface roughness $\sigma$ can be determined. This essentially constitutes the "n&k" method.

For a pure crystalline material, $n=n(\lambda)$ and $k=k(\lambda)$ are distinct quantities, characteristic of the chemical elements comprising the crystal. For a thin film, however, $n=n(\lambda)$ and $k=k(\lambda)$ may depend significantly on various thin-film processes. That is, if the fabrication conditions vary during the thin-film deposition, the microstructure and composition of the film thus produced will change accordingly, which may manifest themselves as changes in the optical properties of the film. Moreover, if further modification processes are introduced to a thin film for purpose of improving its physical properties, $n=n(\lambda)$ and $k=k(\lambda)$ will change accordingly. As such, $n=n(\lambda)$ and $k=k(\lambda)$, along with other physical parameters given by the "n&k" method, serve as sensitive "indicators" of the underlying fabrication and modification processes taking place in various thin films.

In view of the forgoing, the present invention provides a method for monitoring a modifying-process taking place in a thin-film sample and thereby characterizing the sample thus modified. The method of the present invention is carried out as follows: a modifying-process is introduced to a thin-film sample so as to modify and improve physical properties of the sample; an observing spectral range is identified, in which one or more sensitive "n&k" parameters display pronounced changes in response to the modifying-process; and these sensitive "n&k" parameters are then used to monitor the modifying-process and thereby characterize the effects of the modifying-process on the physical properties of the sample.

In this specification and appending claims, a modifying-process should be construed as a process carried out in a thin-film sample for purpose of modifying and improving one or more properties of the sample, such as, but not limited to, physical properties. The "n&k" parameters include index of refraction n, extinction coefficient k, thickness d, energy band-gap $E_g$, and interface roughness $\sigma$ of the sample, as determined by the "n&k" method.

The modifying-process described above can be a curing process in a thermal-activated polymer film, such as a SiLK dielectric film. As a way of example to demonstrate the utility of the present invention, FIG. 1 shows a plot 10 of extinction coefficient k 11 as a function of wavelength $\lambda$ 12 in the ultra-violet (UV) spectral range for six SiLK dielectric films 13, wherein SiLK films 13 have undergone different curing processes characterized by varying curing temperatures 14 and curing times 15 as shown in the FIG. 1. As a result, the spectra 16 of extinction coefficient $k=k(\lambda)$ increases markedly with the curing temperature and curing time, as illustrated in FIG. 1 by 16 A–F.

TABLE I summarizes the physical properties of the six SiLK dielectric film described above. In addition, energy band-gap $E_g$ of the SiLK dielectric films also displays robust and unambiguous changes with the curing temperature and curing time. As such, the energy band-gap $E_g$ and extinction coefficient k provide particularly sensitive "indicators" of the underlying curing processes in the SiLK dielectric films.

TABLE I

Summary of the physical properties determined of the six SiLK dielectric film described in FIG. 1.

| Slot | Cure Temp./Time | Thickness (nm) | Band Gap $E_g$ (eV) | Extinction Coefficient k (330 nm) | Index of Refraction n (314 nm) |
|---|---|---|---|---|---|
| 2 | 320° C./90 s | 513.3 | 3.86 | 0.009 | 1.969 |
| 6 | 420° C./120 s | 518.8 | 3.77 | 0.025 | 1.925 |
| 12 | 440° C./120 s | 519.2 | 3.70 | 0.034 | 1.910 |
| 13 | 440° C./120 s | 519.1 | 3.69 | 0.034 | 1.909 |
| 14 | 440° C./120 s | 520.0 | 3.70 | 0.033 | 1.912 |
| 22 | 470° C./120 s | 520.7 | 3.62 | 0.046 | 1.900 |

The method of the present invention provides many advantages. First, it would be more informative to monitor a modifying-process taking place in a thin-film sample by way of the spectra of index of refraction n and extinction coefficient k, as opposed to n and k at a particular wavelength. This is due to the fact that a thin-film process (such as a thermal-activated polymerization process taking place in a SiLK dielectric film) typically affects the structure of the thin film (e.g., the density and thickness of the SiLK film). Second, given that extinction coefficient k is intimately related to an optical absorption edge of the sample, it serves as a more sensitive and robust indicator for many thin-film processes. Moreover, energy band-gap $E_g$ is a more fundamental measure of the material properties; and in the case of a thermal-activated polymer film, it relates to the physical chemistry of the underlying polymerization process. Third, an assortment of the "n&k" parameters can be obtained by using only a single measurement tool (such as reflectance or transmittance), in contrast to two (or more) simultaneous measurement tools used in the prior art. Further advantages of the method of the present invention are manifest in its non-intrusive nature, fast (or real-time) response, robust sensitivity, and versatility in a variety of thin-film processes.

Furthermore, other physical parameters of a sample, such as dielectric constant, can be deduced from the "n&k" parameters. The method of the present invention can be further utilized to monitor how a particular physical parameter that is critical to a particular system varies in a process.

Figure 2:
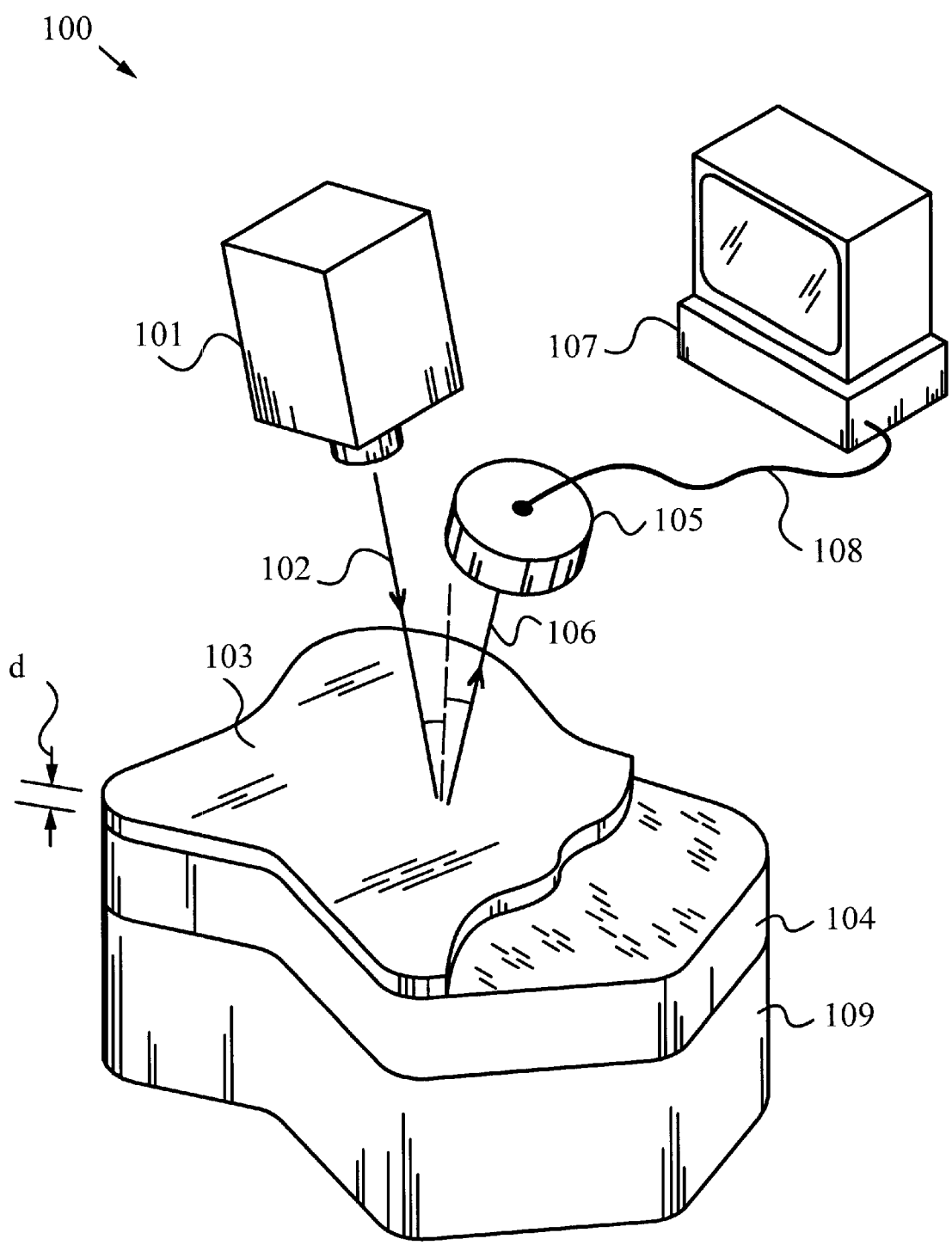
FIG. 2 shows a schematic depiction of an apparatus for monitoring thin-film processes according to the present invention.

FIG. 2 shows a schematic depiction of an apparatus 100 in accordance with the present invention for monitoring a modifying-process taking place in a thin-film sample. Apparatus 100 comprises a light source 101 for delivering an illumination beam 102 onto a thin-film sample 103 disposed on a substrate 104, a detector 105 positioned above thin-film sample 103 for receiving an observation beam 106 emanated from thin-film sample 103, a computing unit 107 connected to detector 105 for processing an optical response 108 transmitted by detector 105, and a device 109 coupled to thin-film sample 103 for introducing a modifying-process thin-film sample 103.

In the above embodiment, light source 101 can be a tunable laser, or any other suitable light source for producing light spanning a spectral range, e.g., from 190 nm to 1000 nm in wavelength. However, the present invention is not limited to this spectral range as it can also be extended from 150 nm to 1700 nm in wavelength. Computing unit 107 can be a personal computer, or any other suitable data processing device. For purpose of illustration, observation beam 106 is shown as a reflected beam; it can also be a transmitted beam. Detector 105 can be a charge-coupled device (CCD), a diode array, or any other suitable light detector that can reliably detect light in the desired wavelength range. From measured observation beam 106, detector 105 derives optical response 108 (e.g., reflectance, or transmittance) and transmits it to computer unit 107.

In operation, thin-film sample 103 is first disposed on substrate 104, by way of spin-coating technique such as in the case of a SiLK dielectric thin film. Light source 101 delivers illumination beam 102 onto thin-film sample 103. Observation beam 106 thus generated is collected by detector 102, and optical response 108 is further transmitted to computer unit 107. Computing unit in turn determines the "n&k" parameters from optical response 108 by way of the "n&k" method.

A person skilled in the art will readily acknowledge and recognize that the above exemplary cases are provided for illustrative purposes of the principle and utility of the present invention, and therefore should not be construed in any way to limiting the scope of the present invention. Those skilled in the art will know how to make use of the present invention for a given application.

Although the present invention and its advantages have been described by way of the above exemplary embodiments, it should be understood that various changes, substitutions, and alterations can be made herein without departing from the principle and the scope of the invention. Accordingly, the scope of the present invention should be determined by the following claims and their legal equivalents.

What is claimed is:

1. A method of characterizing a sample, comprising:
    a) introducing a modifying-process to said sample so as to improve physical properties of said sample;
    b) identifying an observing spectral range, wherein one or more sensitive "n&k" parameters of said sample display pronounced changes in response to said modifying-process; and
    c) using said one or more sensitive "n&k" parameters in combination with Forouhi-Bloomer dispersion equations to monitor said modifying-process and thereby directly characterize said modified sample.

2. The method of claim 1, wherein said one or more sensitive "n&k" parameters are selected from the group consisting of index of refraction n, extinction coefficient k, energy band-gap $E_g$, thickness d, and interfacial coefficient σ.

3. The method of claim 1, wherein said sample comprises a thin film.

4. The method of claim 3, further comprising the step of depositing said thin film on a substrate, before carrying out said step a).

5. The method of claim 1, wherein said sample comprises a thermal-activated polymer film.

6. The method of claim 5, wherein said sample is selected from the group consisting of SiLK dielectric thin films, poly aromatic ethers, and aromatic hydrocarbons.

7. The method of claim 5 wherein said modifying-process is a thermal-curing process, controlled by a curing temperature and a curing time.

8. The method of claim 5, wherein said observation spectral range is in the ultra-violet range.

9. The method of claim 5, wherein said one or more sensitive "n&k" parameters include an extinction coefficient k and an energy band-gap $E_g$ of said thermal-activated polymer film.

10. The method of claim 1, wherein said observing spectral range is selected from a spectrum extending in wavelength from 150 nm to 1700 nm.

11. The method of claim 10, wherein said step b) further comprises the step of identifying an optimal wavelength within said observing spectral range, wherein said changes of said one or more "n&K" parameters at said optimal wavelength is most pronounced.

12. The method of claim 1, further comprising the step of deducing at least one additional physical parameter of said sample from said one or more sensitive "n&k" parameters, thereby monitoring said additional physical parameter in said modifying process.

13. The method of claim 12, wherein said at least one additional physical parameter is a dielectric constant of said sample obtained by extrapolation of $\lambda \to \infty$.

14. An apparatus for characterizing a modifying-process taking place in a thin-film sample, comprising:
  a) a light source for delivering an illuminating beam with a wavelength in an observing spectral range onto said thin-film sample;
  b) a detector for collecting an observation beam emanated from said thin-film sample and deriving an optical response from said observation beam;
  c) a computing unit in communication with said detector for directly determining one or more "n&k" parameters from said optical response in combination with Forouhi-Bloomer dispersion equations; and
  d) a modifying-means for introducing a modifying-process to said thin-film sample.

15. The apparatus of claim 14, wherein said one or more "n&k" parameters are selected from the group consisting of index of refraction n, extinction coefficient k, energy gap Eg, and thickness d.

16. The apparatus of claim 14, wherein said observation beam comprises a reflected beam.

17. The apparatus of claim 16, wherein said optical response comprises a reflectance.

18. The apparatus of claim 14, wherein said observation beam comprises a transmitted beam.

19. The apparatus of claim 18, wherein said optical response comprises a transmittance.

20. The apparatus of claim 14, wherein said thin-film sample comprises a thermal-activated polymer film, and wherein said observing spectral range is in the UV spectral range.

21. The apparatus of claim 20, wherein said thin-film sample is a SiLK dielectric thin film, and wherein said observing spectral range is in a wavelength range of 310–370 nm.

22. The apparatus of claim 14, further comprising a deposition means for depositing said thin-film sample onto a substrate.

* * * * *